United States Patent [19]
Swaminathan et al.

[11] Patent Number: 6,080,140
[45] Date of Patent: Jun. 27, 2000

[54] INTEGRAL CEREBRO-VASCULAR ACCESS SYSTEM

[75] Inventors: M. J. Swaminathan, Dallas, Tex.; Atul Mathur, New Delhi, India

[73] Assignee: Iowa-India Investments Company, Ltd., Douglas, United Kingdom

[21] Appl. No.: 09/185,537

[22] Filed: Nov. 4, 1998

[51] Int. Cl.[7] .................................................. A61M 25/00
[52] U.S. Cl. ....................... 604/500; 604/530; 604/523; 606/108
[58] Field of Search ........................... 604/500, 507, 604/508, 509, 523, 525, 528, 529, 530, 532, 264; 606/108; 600/585, 433–435

[56] References Cited

U.S. PATENT DOCUMENTS

| | | | |
|---|---|---|---|
| 4,895,564 | 1/1990 | Farrell | 604/164 |
| 4,976,689 | 12/1990 | Buchbinder et al. | 604/95 |
| 4,994,027 | 2/1991 | Farrell | 604/53 |
| 5,234,407 | 8/1993 | Teirstein et al. | 604/53 |
| 5,290,226 | 3/1994 | Paskar | 604/530 X |
| 5,531,718 | 7/1996 | Sachse | 604/530 |
| 5,558,635 | 9/1996 | Cannon | 604/49 |
| 5,603,704 | 2/1997 | Brin et al. | 604/264 X |
| 5,619,993 | 4/1997 | Lee | 604/500 X |
| 5,891,057 | 4/1999 | Chaisson et al. | 600/585 |

*Primary Examiner*—John D. Yasko
*Attorney, Agent, or Firm*—Pennie & Edmonds LLP

[57] ABSTRACT

A system and method for percutaneous access to a blood vessel is disclosed. The system according to the present invention includes a flexible guide wire for guiding the system to a desired position in a blood vessel; a tubular member having a lumen sized to slidingly receive the guide wire; an introducer having a lumen sized to slidingly receive the tubular member and a distal section including a S-shaped curve for assisting in positioning the system in the blood vessel; and a sheath having a lumen sized to slidingly receive the introducer, wherein the sheath provides access to the blood vessel after the system has been advanced to the desired position in the blood vessel.

20 Claims, 4 Drawing Sheets

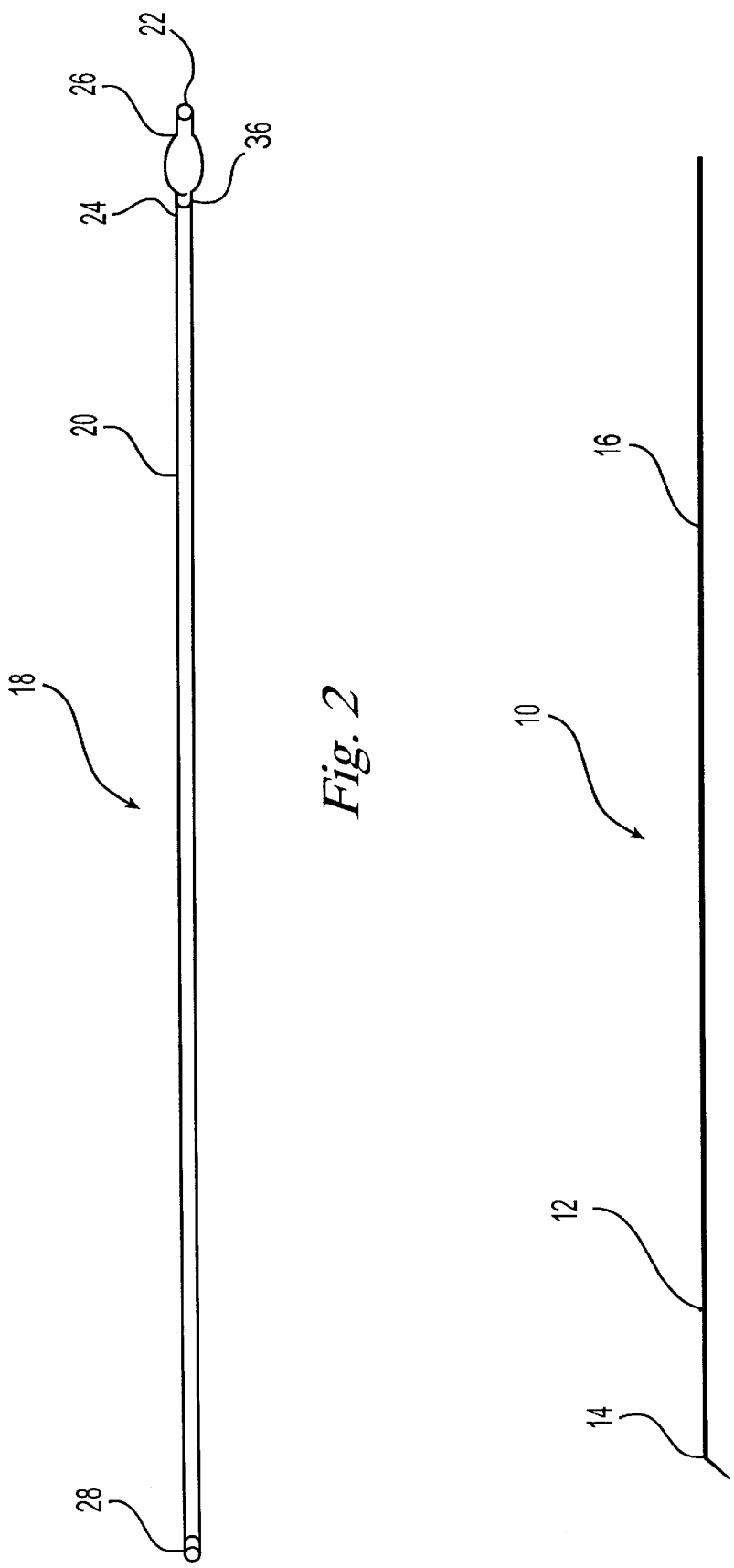

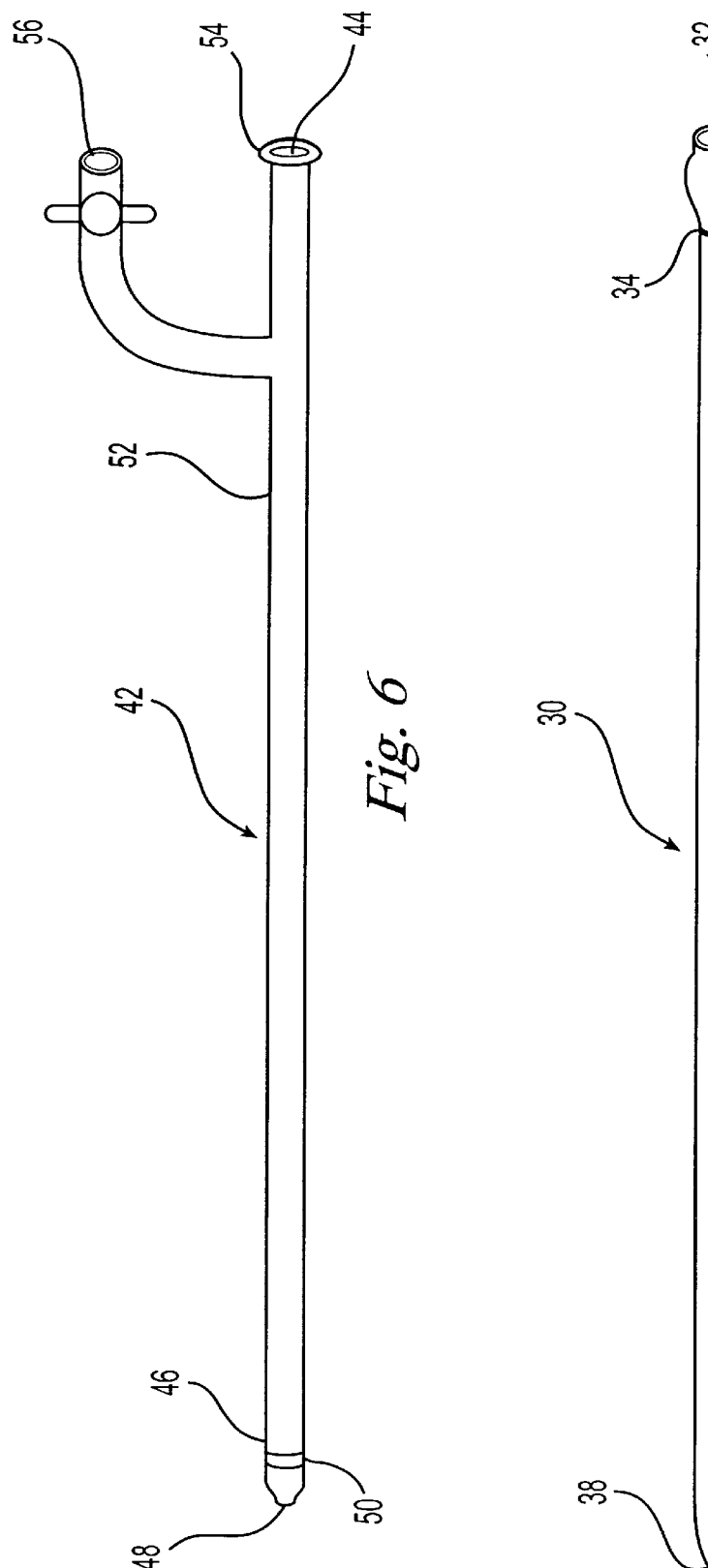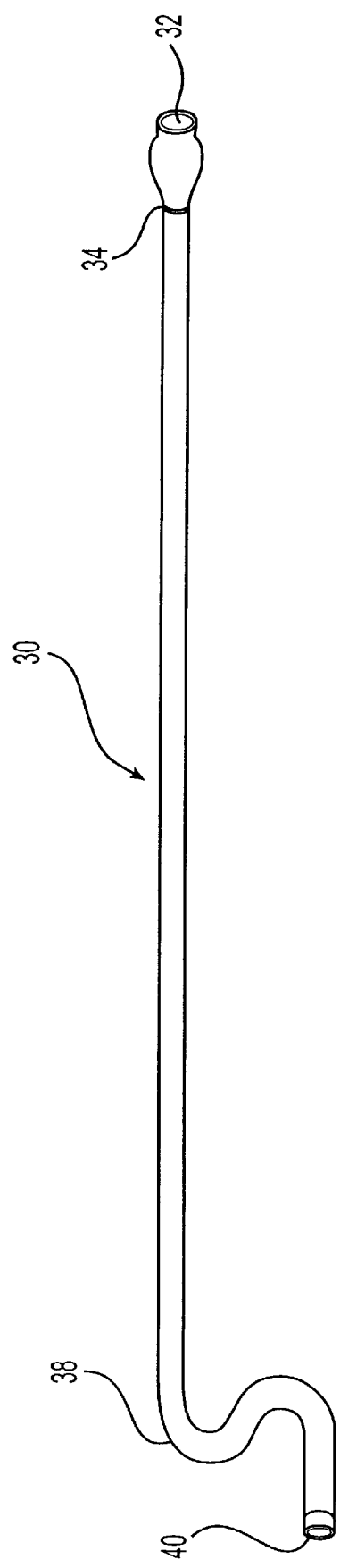

6,080,140

INTEGRAL CEREBRO-VASCULAR ACCESS SYSTEM

FIELD OF THE INVENTION

The present invention is directed to a system and method for access to a blood vessel, and in particular to a system and method for percutaneous access to a cerebral vessel.

BACKGROUND OF THE INVENTION

Any narrowing in the arteries which transport blood to the brain can result in a stroke due to impeded blood flow. Stroke is potentially very damaging to the function of the brain and could lead to paralysis or death. It is the third most common cause of death and the most common cause of disability in the developed world.

Traditional treatments of arterial constrictions involve an open surgical procedure in which the artery is exposed and the surgeon clears the blockage using a procedure called endarterectomy. The morbidity and mortality associated with this technique is high. Hence, minimally invasive techniques have been sought to reduce these complications.

One such minimally invasive technique is percutaneous treatment of blood vessels. Since the introduction of balloons, catheters, and stents, percutaneous treatment of vascular diseases has gained in popularity. These devices have revolutionized treatment of diseases associated with the coronary and other vascular beds in the human body. There are products available to access the coronary arteries in the heart and also the peripheral arteries in the leg through a puncture which is usually made in the femoral artery. Through this puncture, various sheaths, guide wires, guiding catheters are introduced to access a particular section of the artery to be treated using a balloon or a stent.

With the recent advent of non-surgical percutaneous techniques of treating cardiovascular disorders, open surgery is being gradually replaced by non-invasive modes of therapy. In the field of cerebro-vascular diseases, the technology developed for percutaneous coronary artery interventions has been adopted for treating cerebral vessels. For example, Gary Roubin and colleagues have developed a new technique of performing percutaneous cartoid and vertebral artery stenting by the femoral artery route. This technique has been described in a 1996 article published in Circulation.

The safety and efficacy of cartoid and vertebral stenting procedures have been well-established. In addition to these extra cranial procedures, a large number of intra-cranial neurovascular interventions are also being performed all over the world. These intra-cranial interventions include procedures like intracranial angioplasty and stenting, embolic occlusion of arterio-venous malformations and aneurysms, and delivery of intracranial drugs and radiotherapy. A critical part in all of these procedures is obtaining access to the carotid and vertebral arteries by means of guide catheters.

Currently, access to the artery to be treated is obtained by first puncturing the femoral artery in the groin by the Seldinger's technique. A 6 French short sheath is then placed in the created puncture wound. A 5 French diagnostic catheter with a soft guide wire is advanced to engage the origin of the vessel to be treated in the aortic arch. The guide wire is then advanced through the common carotid into the external branch. Next, the diagnostic catheter is advanced over the guide wire which is then exchanged for a stiffer wire. The diagnostic catheter is withdrawn and the 6 French sheath in the femoral artery is also removed.

A long sheath is introduced over the stiff wire and positioned in the carotid artery just proximal to the stenosis. This consists of an outer sheath and a straight introducer tube. The introducer tube is withdrawn once the sheath is placed proximal to the stenosis.

Because the equipment being used for performing carotid and vertebral artery stenting was not originally designed for use in these vessels, there are several deficiencies encountered by interventionists. The most notable of such problems is the lack of an optimal access system. The previously described access procedure is a very lengthy process involving exchange of several guide wires and catheters to obtain access to these supra-aortic vessels. The performance of this complex wire and catheter exchange prolongs the duration of the procedure and also restricts this procedure to only a few experienced interventionists. Even in the hands of an experienced interventionists, vascular anatomical variations make percutaneous treatment of cerebral vessels difficult. There is a risk of air embolism into the cerebral artery in which the exchange takes place. Furthermore, in some cases failure to obtain access to the diseased site leads to an inter-procedural abandonment of the percutaneous technique before treatment.

Thus, there exists a need for an integral access system and method designed specifically for use in the supra-aortic vessels to enhance the ease of the procedure and also ensure greater success of the procedures.

SUMMARY OF THE INVENTION

The present invention relates to a system for obtaining access to a blood vessel. The system according to the present invention comprises a flexible guide wire for guiding the system to a desired position in a blood vessel; a tubular member having an outer surface, an inner surface, and a lumen configured and dimensioned to slidingly receive the guide wire therein; an introducer having a lumen configured and dimensioned to slidingly receive the tubular member therein and a distal section including a S-shaped curve for assisting in positioning the system in the blood vessel; and a sheath having a lumen configured and dimensioned to slidingly receive the introducer therein, wherein the sheath provides access to the blood vessel after the system has been advanced to the desired position in the blood vessel.

The flexible guide wire has a distal tip and a body with the distal tip substantially more flexible than the guide wire body. The distal tip of the guide wire is radiopaque for radiographic visualization for placement of the guide wire. An outer surface of the guide wire has a coating for facilitating sliding movement of the guide wire in the lumen of the tubular member. Preferably, the coating is a hydrogel or PTFE.

The tubular member has a hub at a proximal end for manipulation thereof. The inner surface of the tubular member has a hydrogel coating for facilitating movement of the guide wire in the lumen. Preferably, the hydrogel coating is wetted with a fluid to reduce frictional resistance of the inner surface. The outer surface of the tubular member is made of a polymer for enhancing radial strength. The tubular member has a distal tip that is radiopaque for radiographic visualization of placement of the tubular member.

A distal tip of the introducer is sufficiently soft to enable deflection of the tip into a mouth of the blood vessel. The S-shaped curve of the distal section of the introducer comprises a first curved segment and a second curved segment, with the second curved segment approximately three times as long as the first curved segment. Preferably, the first curved segment comprises two portions oriented at an angle of approximately 70°. In another preferred embodiment, the second curved segment comprises two portions oriented at an angle of approximately 140°.

The introducer comprises a thin layer of PTFE covered by a thin metal braid, and a polyamide coating deposited on the PTFE and metal braid for improving kink resistance of the introducer. The system also includes a locking mechanism for securing the tubular member to the introducer.

The distal part of the sheath has a tapered end for assisting in the introduction of the sheath into the blood vessel. The distal part of the sheath has a distal tip that is radiopaque for radiographic visualization of placement of the sheath. The sheath has a proximal part with a Touhy Borst for accessing the lumen of the sheath and a side port for flushing the lumen of the sheath.

The present invention also relates to a method for accessing a supra-aortic blood vessel of a patient. The method according to the present invention comprises the steps of: creating a femoral artery puncture; inserting the system according to the present invention into the puncture by advancing the guide wire through the femoral artery puncture to the patient's aorta; positioning the tubular member, the introducer, and the sheath over the guide wire; advancing the tubular member, the introducer, and the sheath over the guide wire until the patient's arch of the aorta is reached; advancing the introducer until the S-shaped curved distal end engages the mouth of a supra-aortic blood vessel; advancing the guide wire into the supra-aortic blood vessel; pushing the tubular member and then the sheath into the supra-aortic blood vessel with support from the guide wire; and withdrawing the guide wire, the tubular member, and the introducer to allow the sheath to access the supra-aortic blood vessel.

BRIEF DESCRIPTION OF THE DRAWINGS

FIG. 1 is a side view of a guide wire according to the present invention;

FIG. 2 is a side view of an inner tube according to the present invention;

FIG. 3 is a side view of an introducer according to the present invention;

FIG. 6 is a side view of a sheath according to the present invention; and

DESCRIPTION OF THE PREFERRED EMBODIMENTS

Figure 4:
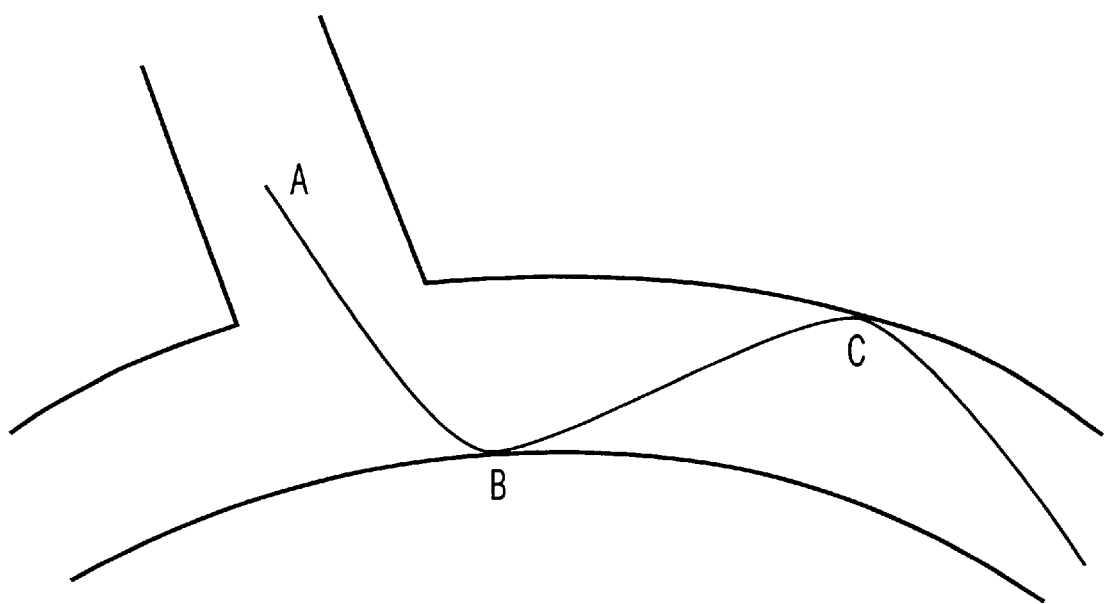
FIG. 4 is a first schematic view of a distal section of the introducer.

The system according to the present invention includes a guide wire 10 as shown in FIG. 1. In use, guide wire 10 guides the other components of the system to the blood vessel to be treated. As the blood vessel to be treated is often different than the blood vessel entered from the skin, guide wire 10 is flexible enough so that it can bend to enter the desired vessel from an entry vessel. However, guide wire 10 has sufficient stiffness so that it can be advanced far from the point of entry. A distal end 12 of guide wire 10 has a floppy tip 14, i.e. a tip that is more flexible than the rest of guide wire 10. Providing guide wire 10 with floppy tip 14 ensures that guide wire 10 has stiffness to enhance the distance that it can be advanced from the point of entry while also ensures that guide wire 10 can bend to enter the blood vessel.

Floppy tip 14 is radiopaque so that the placement of guide wire 10 can be determined and monitored with radiographic visualization instrumentation such as fluoroscopy. As guide wire 10 needs to move freely within blood vessels (either independently or while encompassed by another component of the system according to the present invention) an outer surface 16 of guide wire 10 has a slippery coating such as a hydrogel or a fluorinated polymer such as PTFE. Although guide wire 10 can be sized to suit a particular application, if guide wire 10 is used for cerebral vascular applications, guide wire 10 is preferably 200 cm in length and has a diameter of 0.035 inches.

The system also includes an inner tube 18 as shown in FIG. 2. Inner tube 18 has an outer surface 20, an inner surface (not shown), and a lumen 22. Lumen 22 is configured and dimensioned to receive guide wire 10 in such a fashion that guide wire 10 and inner tube 18 can freely slide with respect to each other while guide wire 10 is in lumen 22. The inner surface of inner tube 18 has a hydrogel coating to facilitate movement of guide wire 10 in lumen 22 of inner tube 18. The lubricating properties of the hydrogel coating can be enhanced by flushing the inner surface of inner tube 18 with saline or other fluids. Outer surface 20 of inner tube 18 also has a slippery coating to allow other components of the system to slip on top of inner tube 18. In order to manipulate inner tube 18 through the various blood vessels, a proximal end 24 of inner tube 18 has a hub 26. A distal end 28 of inner tube 18 is radiopaque so that the placement of inner tube 18 can be determined and monitored with radiographic visualization instrumentation.

In order to improve the radial strength of inner tube 18, outer surface 20 is made of a co-extruded polymer or PTFE. Like guide wire 10, inner tube 18 can be fabricated in different sizes to suit a particular application as long as lumen 22 is large enough to accommodate guide wire 10. For cerebral applications, inner tube 18 is preferably 140 cm in length.

The system according to the present invention also includes an introducer 30 as shown in FIG. 3. A lumen 32 of introducer 30 is configured and dimensioned to receive inner tube 18 in such a fashion that introducer 30 and inner tube 18 can freely slide with respect to each other while inner tube 18 is in lumen 32. In order to secure introducer 30 to inner tube 18 to prevent respective movement, introducer 30 has a locking mechanism 34 that interacts with a corresponding locking mechanism 36 on inner tube 18. A distal section 38 of introducer 30 includes a S-shaped curve for assisting positioning into the mouth of the blood vessel. Distal section 38 terminates in a distal tip 40 which is soft to further facilitate deflection of tip 40 into the mouth of the blood vessel. In order to provide introducer 30 with resistance to kinking without unnecessarily increasing the thickness, introducer 30 is made of a thin layer of PTFE covered by a thin metal braid. A polyamide coating is then deposited on the braided layer.

Figure 5:
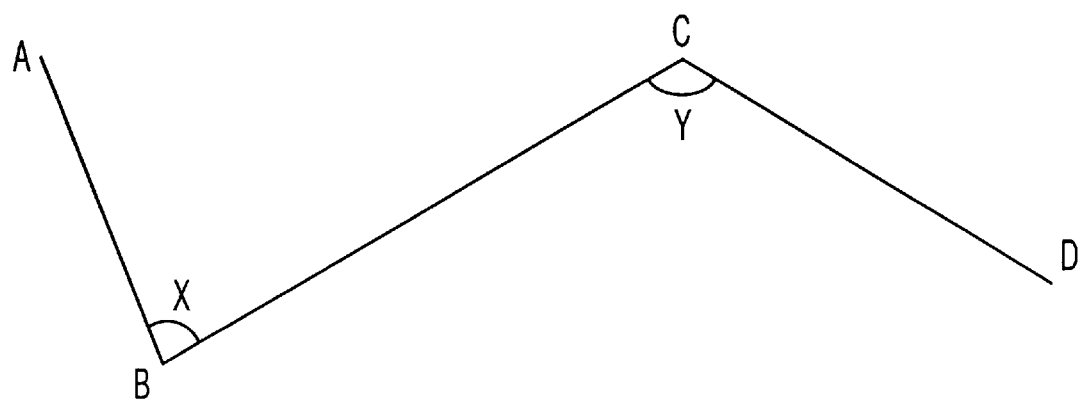
FIG. 5 is a second schematic view of the distal section of the introducer.

Schematic views of distal section 38 of introducer 30 are shown in FIGS. 4 and 5. The S-shaped curve of distal section 38 is comprised of a first curved segment AB connected to a second curved segment BC. Second curved segment BC is approximately three times longer than first curved segment AB. First and second curved segments AB and BC are oriented with respect to each other in such a fashion that angle x formed by lines AB and BC is approximately 70° and angle y formed by lines BC and CD (with D being any point along the rest of introducer 30) is approximately 140°. As described in more detail below, the respective lengths and alignment of first and second curved segments AB and BC are designed to help position and move distal section 38 of introducer 30 into the mouth of the vessel to be treated. Like the other components of the system, introducer 30 can be fabricated in different sizes to suit a particular application as long as lumen 32 is large enough to accommodate inner tube 18. For cerebral applications, introducer 30 is preferably 120 cm in length.

The final component of the system according to the present invention is a sheath 42 shown in FIG. 6. After guide wire 10, inner tube 18, and introducer 30 have been advanced to the desired location on the blood vessel to be treated, sheath 42 provides access for the minimally invasive procedure. Sheath 42 has lumen 44 configured and dimensioned to receive introducer 30 in such a fashion that introducer 30 and sheath 42 can freely slide with respect to each other while introducer 30 is in lumen 44.

A distal part 46 of sheath 42 has a soft and tapered end 48 for assisting introduction of sheath 42 into the blood vessel. Distal part 46 also includes a marker 50 that is radiopaque for radiographic visualization of the placement of sheath 42. A proximal part 52 of sheath 42 has a Touhy Borst 54 for accessing lumen 44 and a side port 56 for flushing lumen 44. Like the other components of the system, sheath 42 can be fabricated in different sizes to suit a particular application as long as lumen 44 is large enough to accommodate introducer 30. For cerebral applications, sheath 42 is preferably 110 cm in length.

Figure 7:
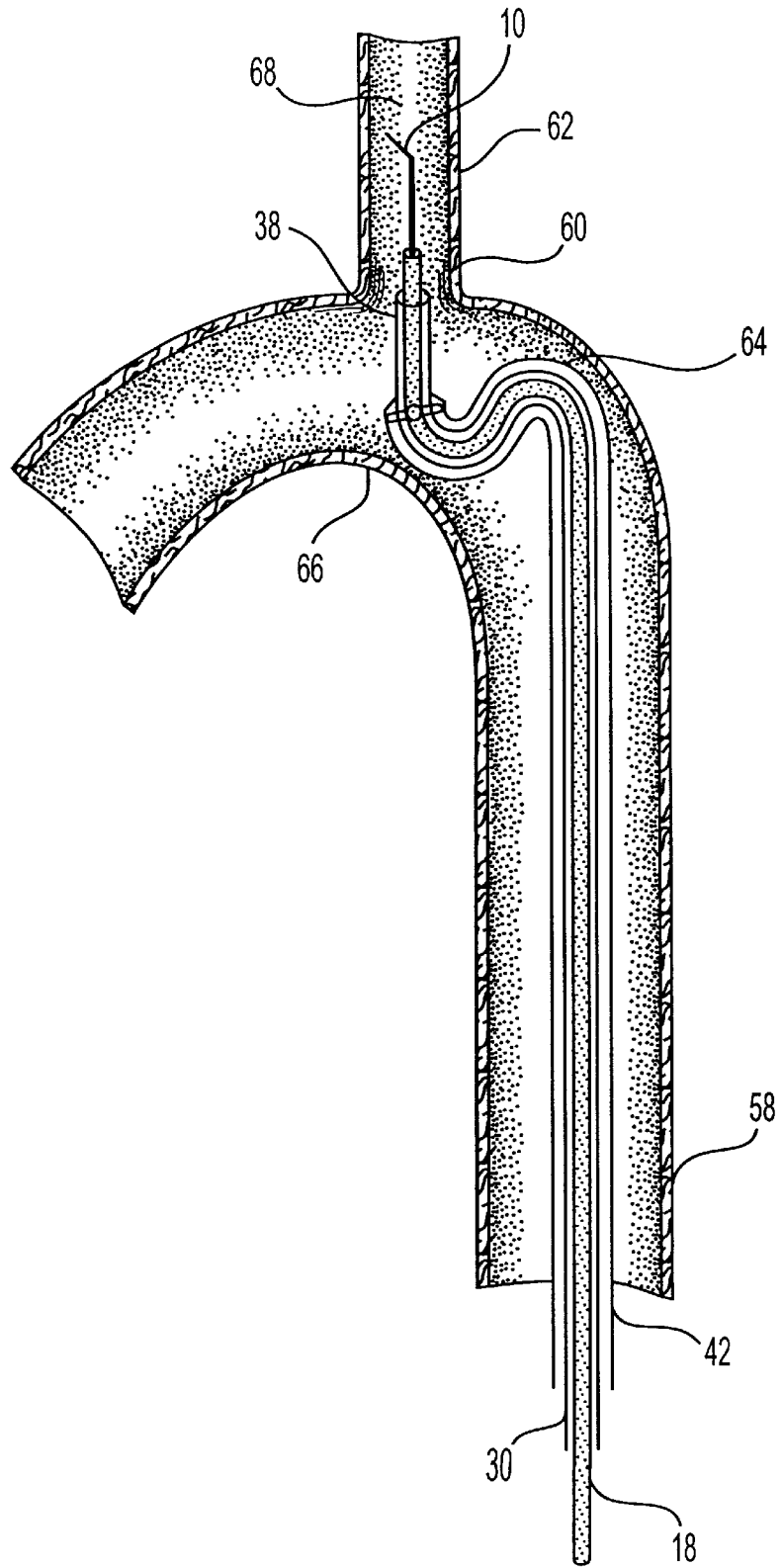
FIG. 7 is a sectional view of the system according to the present invention inserted in a supra-aortic blood vessel.

Although the system according to the present invention can be used for a number of different applications, a method of using the system will be described using the carotid artery as an example. A femoral artery puncture is made using any known procedure such as Seldinger's technique. As shown in FIG. 7, guide wire 10 is inserted into aorta 58. Introducer 30, inner tube 18, and sheath 42 are then positioned over guide wire 10 until aorta 58 is reached. Introducer 30 is advanced until-distal section 38 engages mouth 60 of carotid artery 62. Because of the S-shaped curve of distal section 38, introducer 30 deflects from aortic arch 64 and aortic base 66 and into mouth 60 of carotid artery 62 as introducer is advanced up aorta 58. Guide wire 10 is then advanced into external branch 68 of carotid artery 62. Inner tube 18 is pushed forward so that sheath 42 can be advanced using the support of guide wire 10 and inner tube 18. Finally, guide wire 10, inner tube 18, and introducer 30 are withdrawn so that lumen 44 of the sheath can be used as a conduit to perform the desired procedure.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A system for obtaining access to a blood vessel comprising:
    a flexible guide wire for guiding the system to a blood vessel;
    a tubular member having an outer surface, an inner surface, and a lumen configured and dimensioned to slidingly receive the guide wire therein;
    an introducer having a lumen configured and dimensioned to slidingly receive the tubular member therein and a distal section including a S-shaped curve for assisting in positioning the system in the blood vessel; and
    a sheath having a lumen configured and dimensioned to slidingly receive the introducer therein, wherein the S-shaped curve of the distal section of the introducer positions the system in a desired position in a mouth of the blood vessel, the tubular member is configured and positioned to extend past through the introducer and into the blood vessel, and the guide wire, tubular member, and introducer can be removed to allow the sheath to thereafter provide access to the blood vessel after the system has been advanced to the desired position in the blood vessel.

2. The system of claim 1 wherein the flexible guide wire has a distal tip and a body with the distal tip being substantially more flexible than the guide wire body.

3. The system of claim 1 wherein the flexible guide wire has a distal tip that is radiopaque for radiographic visualization of placement of the guide wire.

4. The system of claim 1 wherein an outer surface of the flexible guide wire has a coating for facilitating sliding movement of the guide wire in the lumen of the tubular member.

5. The system of claim 4 wherein the coating is a hydrogel or a fluorinated polymer.

6. The system of claim 1 wherein the tubular member has a hub at a proximal end for manipulation thereof.

7. The system of claim 1 wherein the inner surface of the tubular member has a coating for facilitating movement of the guide wire in the lumen.

8. The system of claim 7 wherein the coating comprises a hydrogel which is wetted with a fluid to reduce frictional resistance of the inner surface.

9. The system of claim 1 wherein the outer surface of the tubular member is made of a polymer for enhancing radial strength.

10. The system of claim 1 wherein the tubular member has a distal tip that is radiopaque for radiographic visualization of placement of the tubular member.

11. The system of claim 1 wherein a distal tip of the introducer is sufficiently soft to enable deflection of the tip into a mouth of the blood vessel.

12. A system for obtaining access to a blood vessel comprising:
    a flexible guide wire for guiding the system to a blood vessel;
    a tubular member having an outer surface, an inner surface, and a lumen configured and dimensioned to slidingly receive the guide wire therein;
    an introducer having a lumen configured and dimensioned to slidingly receive the tubular member therein and a distal section including a S-shaped curve for assisting in positioning the system in the blood vessel; and
    a sheath having a lumen configured and dimensioned to slidingly receive the introducer therein,
    wherein the S-shaped curve of the distal section of the introducer comprises a first curved segment extending in a first direction and having a flexible tip for facilitating deflection into a mouth of the blood vessel and a second curved segment extending in a second direction different from the first direction, with the second curved segment being approximately three times as long as the first curved segment and
    wherein the S-shaped curve of the distal section of the introducer positions the system in the desired position in the mouth of the blood vessel, and the guide wire and tubular member can be removed to allow the sheath to thereafter provide access to the blood vessel after the system has been advanced to the desired position in the blood vessel.

13. The system of claim 12 wherein the first curved segment comprises two portions oriented at an angle of approximately 70°.

14. The system of claim 12 wherein the second curved segment comprises two portions oriented at an angle of approximately 140°.

15. The system of claim 1 wherein the introducer comprises a layer of a fluorinated polymer covered by a metal braid, and a polyamide coating deposited on the metal braid for improving kink resistance of the introducer.

16. The system of claim 1 further comprising a locking mechanism for securing the tubular member to the introducer.

17. The system of claim 1 wherein the distal part of the sheath has a tapered end for assisting in the introduction of the sheath into the blood vessel.

18. The system of claim 1 wherein the distal part of the sheath has a distal tip that is radiopaque for radiographic visualization of placement of the sheath.

19. The system of claim 1 wherein the sheath has a proximal part with a Touhy Borst for accessing the lumen of the sheath and a side port for flushing the lumen of the sheath.

20. A method for accessing a supra-aortic blood vessel of a patient comprising the steps of:

creating a femoral artery puncture;

inserting the system of claim 1 into the puncture by advancing the guide wire through the femoral artery puncture to the patient's aorta;

advancing the tubular member, the introducer, and the sheath over the guide wire until the patient's aorta is reached;

advancing the introducer until the S-shaped curved distal end engages a mouth of the supra-aortic blood vessel;

advancing the guide wire and the tubular member into the supra-aortic blood vessel;

pushing the sheath into the supra-aortic blood vessel with support from the guide wire and the tubular member; and withdrawing the guide wire, the tubular member, and the introducer to allow the sheath to access the supra-aortic blood vessel.

* * * * *